US006477425B1

(12) United States Patent
Nowick et al.

(10) Patent No.: US 6,477,425 B1
(45) Date of Patent: Nov. 5, 2002

(54) EXTERNAL TRANSMITTER FOR IMPLANTED MEDICAL DEVICE

(75) Inventors: Matthew Nowick, Iowa City, IA (US); James Malaney, Iowa City, IA (US)

(73) Assignee: MMC/GATX Partnership No. 1, Lafayette, CA (US)

( * ) Notice: Subject to any disclaimer, the term of this patent is extended or adjusted under 35 U.S.C. 154(b) by 0 days.

(21) Appl. No.: 09/472,071

(22) Filed: Dec. 23, 1999

(51) Int. Cl.$^7$ .............................. A61N 1/02; H02J 17/00
(52) U.S. Cl. ............................................ 607/61; 607/60
(58) Field of Search ............................. 607/61, 60, 32, 607/33, 16, 3, 31, 40, 41, 46; 128/902, 903

(56) References Cited

U.S. PATENT DOCUMENTS

| | | | | |
|---|---|---|---|---|
| 4,679,560 A | * | 7/1987 | Galbraith | 128/419 |
| 5,094,242 A | | 3/1992 | Gleason et al. | 128/642 |
| 5,211,175 A | | 5/1993 | Gleason et al. | 128/642 |
| 5,306,986 A | * | 4/1994 | Siao | 315/248 |
| 5,314,457 A | * | 5/1994 | Jeutter et al. | 607/116 |
| 5,405,367 A | * | 4/1995 | Schulman et al. | 607/61 |
| 5,755,748 A | * | 5/1998 | Borza | 607/61 |
| 5,891,183 A | | 4/1999 | Zierhofer | 607/57 |
| 6,058,330 A | * | 5/2000 | Borza | 607/61 |
| 6,240,318 B1 | * | 5/2001 | Phillips | 607/61 |

\* cited by examiner

Primary Examiner—Kennedy Schaetzle
(74) Attorney, Agent, or Firm—Dorsey & Whitney LLP; Scott D. Rothenberger

(57) ABSTRACT

An external transmitter assembly for powering and controlling an implanted medical device, wherein a battery drives first and second power supplies that energize a modulation circuit and an amplifier, respectively, to apply programmed current pulses to a transmitting antenna. The second power supply is output limited and couples through holdup capacitors and a filter network to the amplifier, allowing momentary high current operation without affecting oscillator or modulation portions of the circuit. The transmitting antenna has a diameter greater than that of the implanted receiving antenna, and is adhered to the skin of the patient over the implanted device and is tuned by a trimmer element to resonate at the resonant frequency of the receiver and enhance energy coupling between the two coils A local oscillator operating at high frequency is divided down to form a clock, and the pulse-defining modulation circuit includes an FPGA that controls pulse shape and timing regimens for a defined neurologic treatment. The two power supplies have high switching frequencies that are different from each other and from the main transmitter operating frequency to minimize aliasing effects between the units. In addition an auto power-down circuit connects the battery to the power supplies. Upon user actuation of the main power switch, that circuit connects power to boot the FPGA, which then provides a switching enable gate signal; the auto circuit disconnects the battery when the state of the FPGA signal indicates a treatment cycle is over. The auto power down circuit draws little power, thus assuring that battery life is unimpaired if the user forgets to turn off the transmitter, or leaves it in a shut down state for extended periods of time.

5 Claims, 6 Drawing Sheets

EXTERNAL TRANSMITTER FOR IMPLANTED MEDICAL DEVICE

CROSS-REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates to medical devices that are implanted in a body and receive their operating energy from an external source, e.g., a transmitter, without transdermal circuit conductors. It particularly relates to nerve stimulation or conditioning devices in which such external energy is received by an implanted receiving coil and applied to an implanted electrode. Such systems are shown in U.S. Pat. Nos. 5,094,242; 5,211,175 and elsewhere.

The device described in the aforesaid patents is shaped like a thumb tack and has a needle-like electrode structure protruding from a disk-like cap. The cap contains a coil which operates as an energy-receiving antenna, and the coil is inductively energized by an external transmitter that applies an rf frequency signal to a transmitting antenna located proximate to the implanted receiver and outside of the body. In that device, the external transmitter transmits at a frequency to which the internal coil is tuned, to enhance the efficiency of energy coupling through the skin and into the neural stimulation electrode. The two coils effectively act as windings of a transformer coupled by a magnetic field that is created by rf current flow in the external coil.

The nature of this coupling is relatively inefficient, and depends very much on the spacing, position and shape of the respective coils. In general, the magnetic field created by a transmitting coil, and the coupling efficiency between two such coils, requires them to be closely spaced and well aligned or contiguous. It has been suggested in U.S. Pat. No. 5,891,183 that one or both of these coils may employ non-circular windings to enhance the magnetic coupling coefficient between the two coils and make the energy coupling efficiency less sensitive to their relative positioning. For a subcutaneous device such as the device illustrated in U.S. Pat. No. 5,211,175, the receiving coil may reside in a relatively well-defined position at a shallow depth below the skin and it is therefore possible to position the external transmitter fairly close to and roughly in alignment with the receiver. However, coupling efficiency remains a serious factor. If the contemplated neural stimulation regimen requires continuous, repeated or relatively long-term application of electrical stimulation, and battery power is contemplated for the external transmitter, overall efficiency of electrical usage as well as stability of the power source both become important concerns.

It would therefore be desirable to provide an external transmitter assembly that is power efficient.

It would further be desirable to provide an external transmitter assembly that uniformly and dependably couples modulated power to a passive implanted receiver.

SUMMARY OF THE INVENTION

One or more of the foregoing or other desirable ends are achieved in accordance with the present invention by an external transmitter assembly for powering an implanted medical device, wherein a battery drives first and second power supplies that energize a modulation circuit and an amplifier, respectively, to drive an rf coupling antenna. The second power supply is output limited and couples through holdup capacitors to the amplifier, allowing momentary high current operation without affecting rf or pulse modulation portions of the circuit. The transmitting antenna has a diameter greater than that of the implanted receiving antenna, and is adhered to the skin of a patient over the implanted device. The transmitting coil is preferably tuned with a small variable circuit element to resonate at the resonant frequency of the implanted receiver to more effectively couple energy between the two coils. A local oscillator operating at high frequency is divided down to form clock signals for pulse generation, and three distinct high frequency signals provide switching frequencies for the power supplies and a precisely controlled rf transmitter operating frequency. A field programmable gate array (FPGA) powered by the first power supply controls pulse shape and timing regimens for a defined neurologic treatment. By providing the two power supplies with high switching frequencies that are different from each other and from the main transmitter operating frequency, aliasing and power stealing effects between the units are avoided. In addition, an auto power-down circuit connects the battery to the power supplies. That circuit connects battery power upon user actuation of a main power switch, and disconnects the battery when the signal state of an FPGA signal enable line indicates a treatment cycle is over. The auto power-down circuit draws little power, thus assuring that battery life is unimpaired if the user forgets to turn off the transmitter, or leaves it in a shut down state for extended periods of time.

BRIEF DESCRIPTION OF THE DRAWINGS

These and other features of the invention will be understood from the description below, taken together with Figures illustrating embodiments and aspects thereof, wherein.

DETAILED DESCRIPTION

Figure 1:
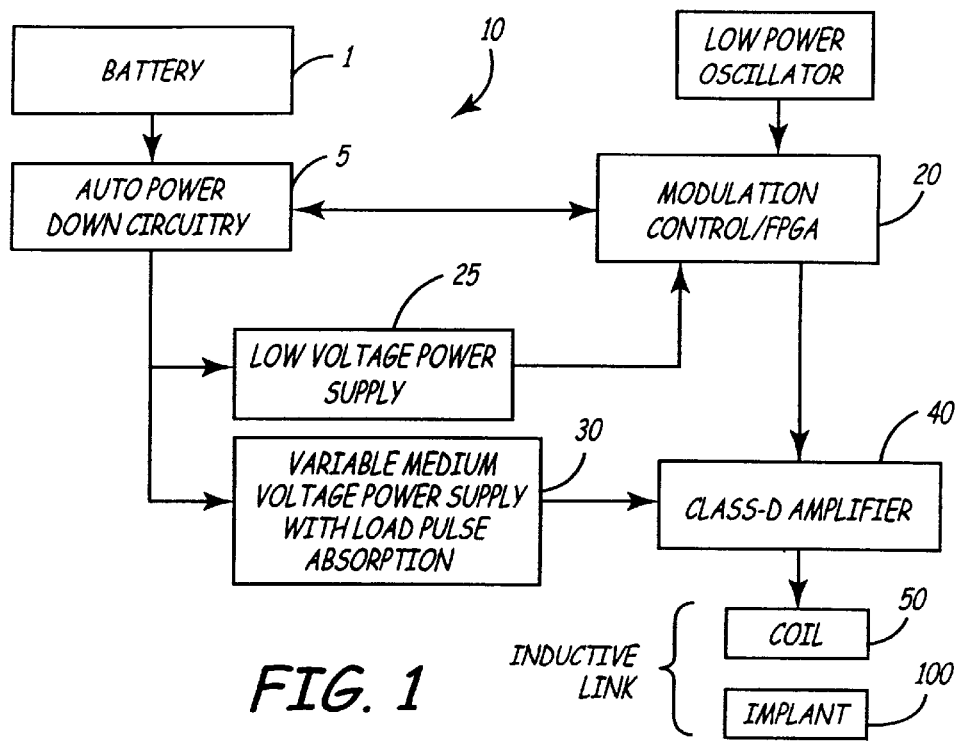
FIG. 1 is a functional block diagram of an external transmitter of the invention.

FIG. 1 shows a functional block diagram of the external transmitter assembly 10 of the present invention which powers an implant 100. As shown, the transmitter 10 employs a battery 1 which couples via an auto power down circuit 5 to the active elements of the transmitter. The auto power down circuit 5 may be initially actuated to turn on the device by a manually operated switch thrown by the user, and it receives a further input from an FPGA 20 indicative of the end of a treatment cycle, at which time it disconnects power independently of the present state of the user switch.

As further shown in FIG. 1, the battery powers a low voltage power supply 25 and a variable medium voltage power supply 30. The low voltage power supply powers the FPGA 20, while the medium voltage supply 30 drives a class D amplifier 40. Amplifier 40 receives an input signal from the FPGA 20 and amplifies it to produce a high powered signal which is applied to the external coil 50 for inductively coupling energy into the implant. Power supply 30 is an output limited power supply, and couples via hold up capacitors and an RC filter network (FIG. 5) to the amplifier 40 allowing amplifier operation at high current pulse levels without impairing operation of the other elements which depend upon power from the small battery supply, which may, for example consist of two AA cells and have limited capacity.

Figure 2:
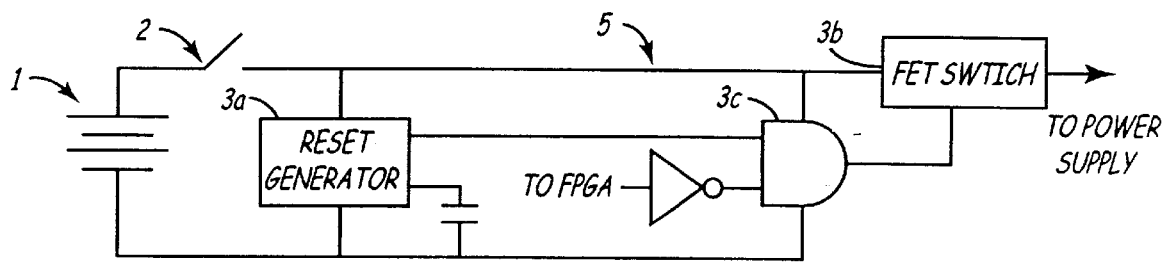
FIG. 2 shows the auto power down circuit of the transmitter of FIG. 1.

FIG. 2 schematically illustrates the construction of the auto power down circuit 5 of the transmitter 10. As shown, the battery 1 is connected via a manually operated switch 2 to a reset generator 3a and to the power terminal of a FET switch 3b. The reset generator 3a generates a fixed reset pulse which through a logic gate 3c forces the FET switch into an ON state. When the FET is on, the main low voltage power supply automatically starts functioning and drives the FPGA which runs through its boot cycle and provides an enable signal through a logic gate to force the FET to remain ON. Thus, if the FPGA does not begin operation within the fixed reset pulse period, the unit will again turn itself off. Once the FPGA has forced the FET ON it will remain on until the end of a treatment cycle at which time the FPGA turns OFF the FET through the logic gate, and the battery power to the unit is turned off. Thus, user actuation of the manual switch 2 is required to turn the unit ON, while either an FPGA signal or a user switch movement can turn the unit OFF. This assures that the unit cannot accidently turn itself ON when the user is not expecting it. In addition, as further described below, a battery life comparator also assures that the circuit operates even when the battery is starting to go dead. The overall circuit is designed to draw so little power that there will be negligible effect on battery life if the user leaves the unit in its shut down state for extended periods of time.

Figure 3:
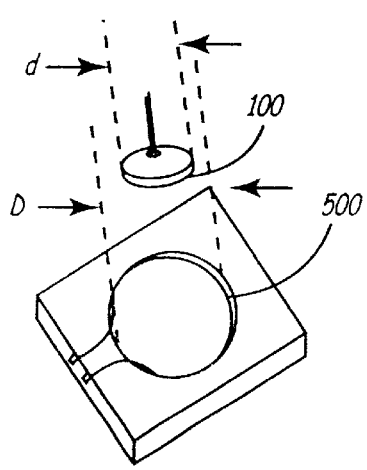
FIG. 3 illustrates a preferred antenna of the external transmitter.

FIG. 3 illustrates in simplified form the preferred configuration of transmitting and receiving coils 50, 100. As shown, the implant 100 has a multi-winding coil which may for example have a diameter of approximately one centimeter. The transmitter coil 50, on the other hand, which is illustrated attached to or housed within a thin adhesive epidermal patch or box, has a diameter greater than that of the implanted coil 100. For example, for use with the one centimeter receiving coil, the coil 50 may have a diameter of 1.5 to 2.5 centimeters, fifty to one hundred fifty percent greater than the diameter of the implanted coil, so that its projected profile forms a band lying roughly several millimeters outside the perimeter of the implanted receiving coil. This has the effect that the transmitter coil is sufficiently small to provide a relatively high magnetic coupling field, while being sufficiently large that it is readily positioned on the surface of the skin with the receiving coil 100 lying within its contour but proximate to the external coil windings. Slight shifting of their relative positions therefore enhances inductive coupling along a portion of the coil circumference to an extent comparable to its decrease in the complementary portion, with the result that coupling efficiency remains both high and relatively constant, even when an eccentricity or misalignment of several millimeters occurs.

Figure 4:
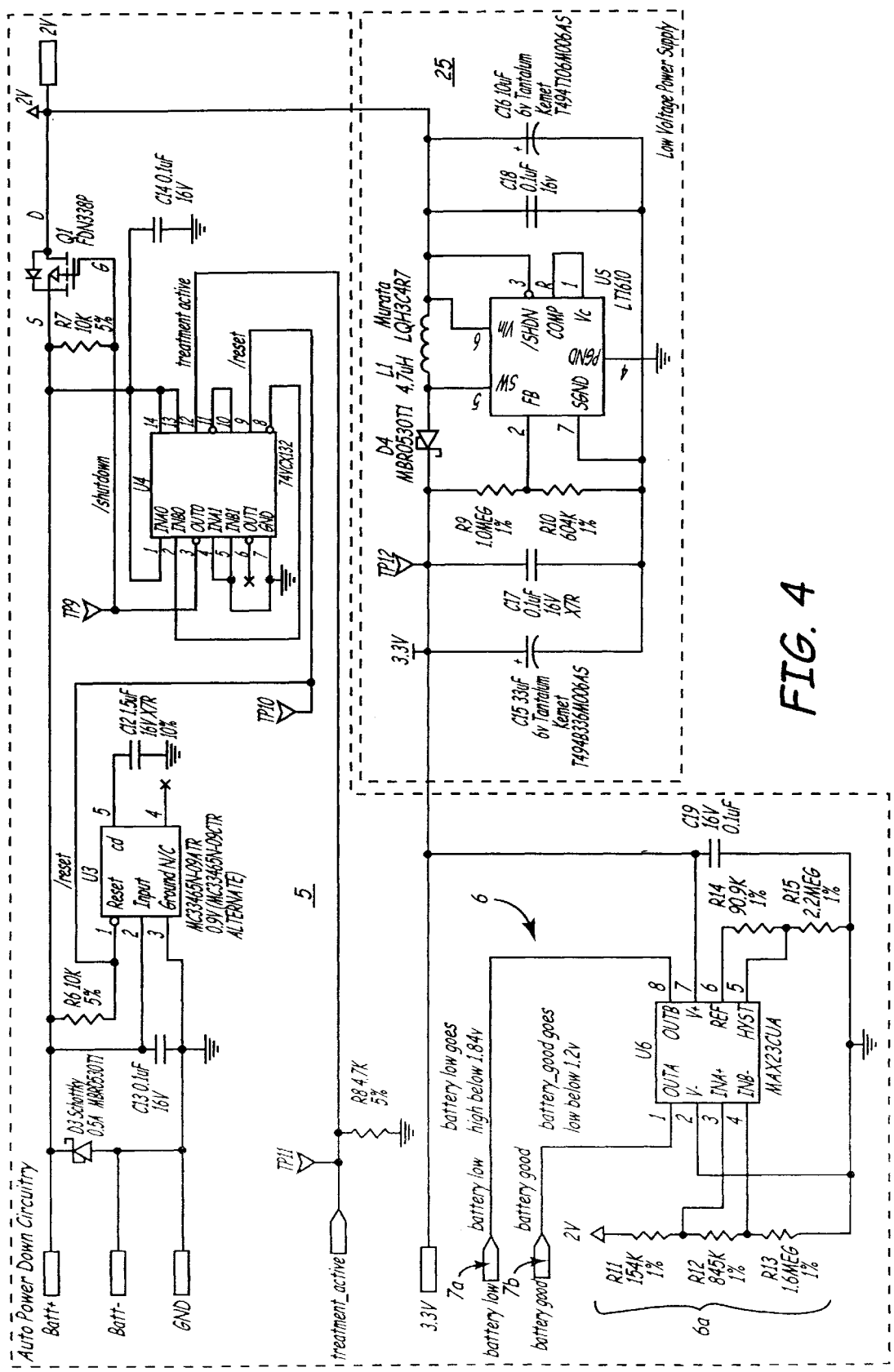
FIG. 4 shows circuitry of the auto power down and low voltage power supply portions of the embodiment of FIG. 1.

In a preferred embodiment of the external transmitter, the circuit elements are configured to be ON and drawing power precisely during intervals of operation required for the functional application of treatment pulses to the vicinity of a nerve or nerve bundle. Thus, the user actuated switch 2 (FIG. 2) connects the battery for the duration of the reset interval set by the reset generator, and during this time the FET switch 3b connects the battery to the low voltage power supply 25 (FIGS. 1 and 4). The programmable gate array then proceeds to define suitable nerve treatment pulse sequences, which are amplified to drive the transmitter coil 50 and thus supply relatively short signals to the implanted nerve stimulation electrode. One typical drive regiment involves a stimulation pulse of duration 50–250 microseconds, applied ten or twenty times per second, either for a few seconds, several minutes, or continuously. The medium voltage power supply 30 is ON during pulse amplification for treatment regimens, at which time it powers the amplifier 40 to create energy pulses which, for application in the vicinity of the sacral nerve for treating urinary incontinence as described in the aforesaid two United States patents, may, for example, apply pulses of 200 microseconds duration at intervals of about 50 milliseconds, either continuously, or for a defined number of times. Other programmed antenna excitation regimens may be provided as appropriate for different nerve treatments and other medical conditions.

Figure 5:
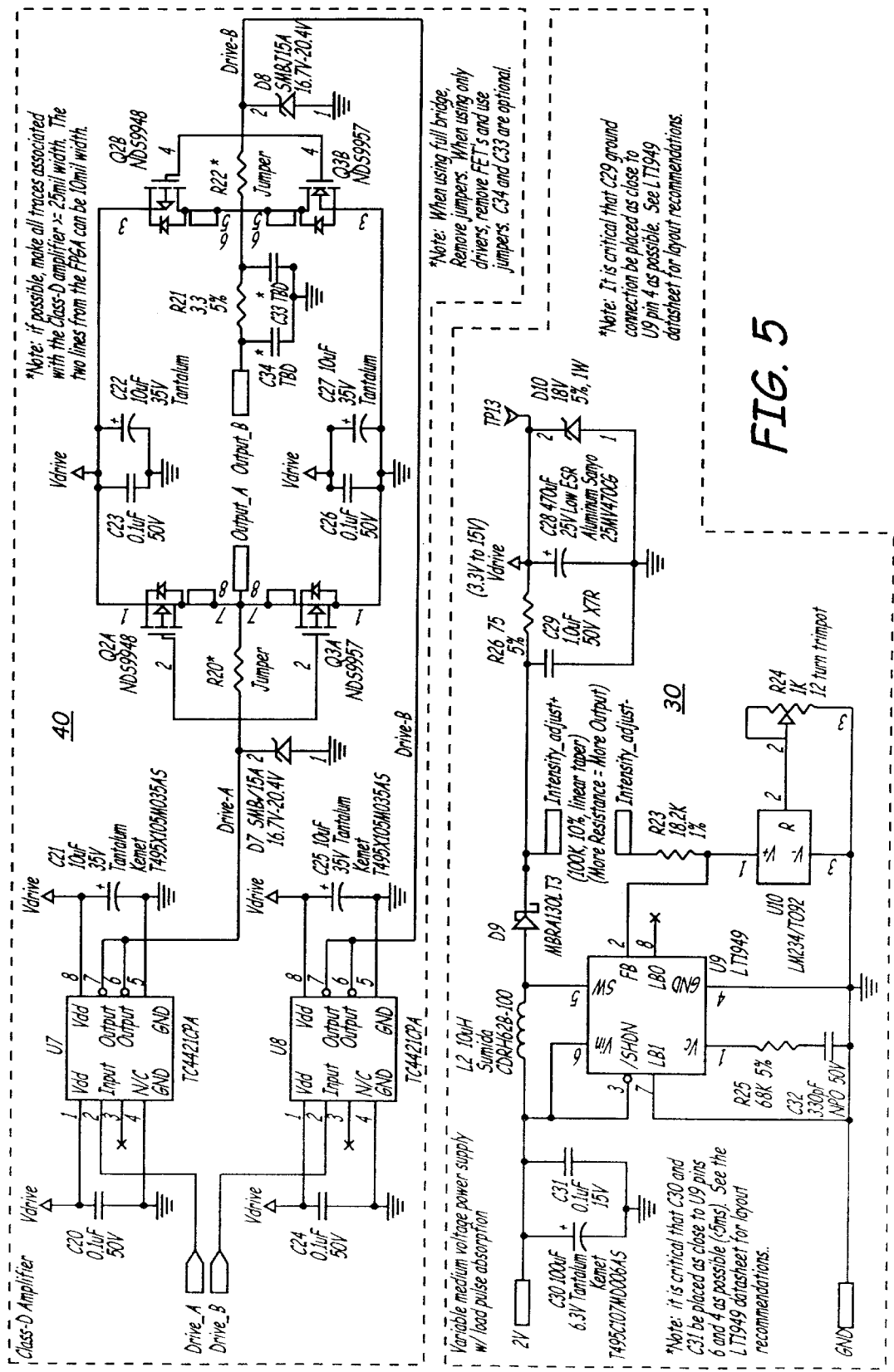
FIG. 5 shows circuitry of the medium voltage power supply and amplifier of the embodiment of FIG. 1.

FIGS. 4 and 5 illustrate circuit elements of the auto power-down circuitry, the power supplies and the amplifier in greater detail. As shown in FIG. 4, the auto power-down circuitry include a battery check section 6 wherein a divider bridge 6a operative on the low voltage line produces threshold voltages for comparison to the battery supply to actuate indicator lights for displaying when the battery is low or ceases to be good. A "battery low" line 7a goes high below a threshold that represents a remaining battery life of approximately ten per cent, while the "battery depleted" line 7b goes low when the voltage drops below a point where the battery voltage is too low to correctly power the device. These outputs connect to the FPGA/modulation control unit 20 (FIG. 5A) which in turn actuates an appropriate indicator LED. By way of example the battery low LED may be an amber LED while more extreme level of depletion may be indicated by blinking actuation, a separate color LED or the like. As described further below, preferably a separate LED is illuminated to indicate when a treatment cycle is in progress.

Figure 6A:
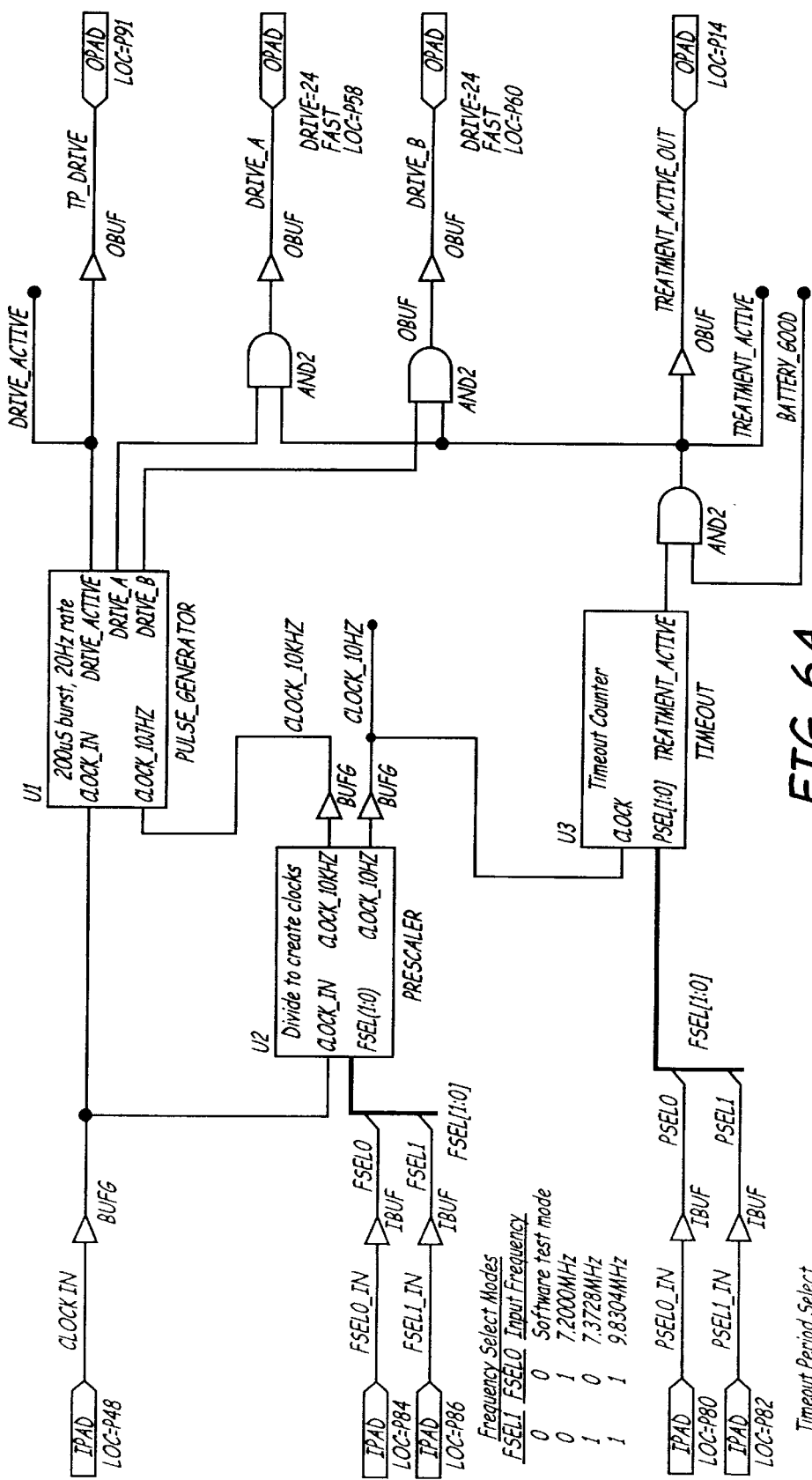
FIGS. 6a and 6b illustrate logic of various timing and pulse forming units defined by the FPGA.

FIG. 5 illustrates the output driver block including the variable medium voltage power supply 30 and the amplifier section 40 of the external transmitter 10. In the power supply, an intensity adjustment potentiometer together with a constant current source adjusts the power output, while capacitors C30 and C31 between the input and ground, and capacitor C29 between the output and ground, stabilize and filter the switching converter, U9. The ground connections of C29 to C31 are placed as close as possible to the grounded pin 4 of circuit element U9, with the other ends of capacitors C30 and C31 positioned as close as possible to the voltage input pin 6 to enhance power limited smooth operation when the amplifier presents a high draw. The filtering resistor, R26, together with C28 absorb large pulse currents. Amplifier 40 operates with parallel drive channels A and B, which as shown connect to a bridge at the output. The channels may be run separately by removing the FETs of the bridge and using simply jumpers R20, R22, or the full bridge may be employed by removing the jumpers. Amplifier 40 is a class D amplifier, i.e., it operates by rapidly switching the drive voltage in accordance with the signals provided at its input terminals and a high frequency switching signal supply. As shown in further detail in FIG. 6A, a two bit state controller selects among the frequencies of 7.2000, 7.3728 and 9.8304 megahertz as appropriate to generate the pulse duration and repetition frequencies and for the transmitter transmitter frequency synthesis. As noted above, applying potentials in the vicinity of sacral region nerve ending, a protocol of high energy pulses of duration approximately 200 microseconds is preferred and the general provision of appropriate timing, timeout and enable signal is provided by the FPGA 20 (FIG. 1) which controls and synchronizes the various units described so far.

Figure 5A:
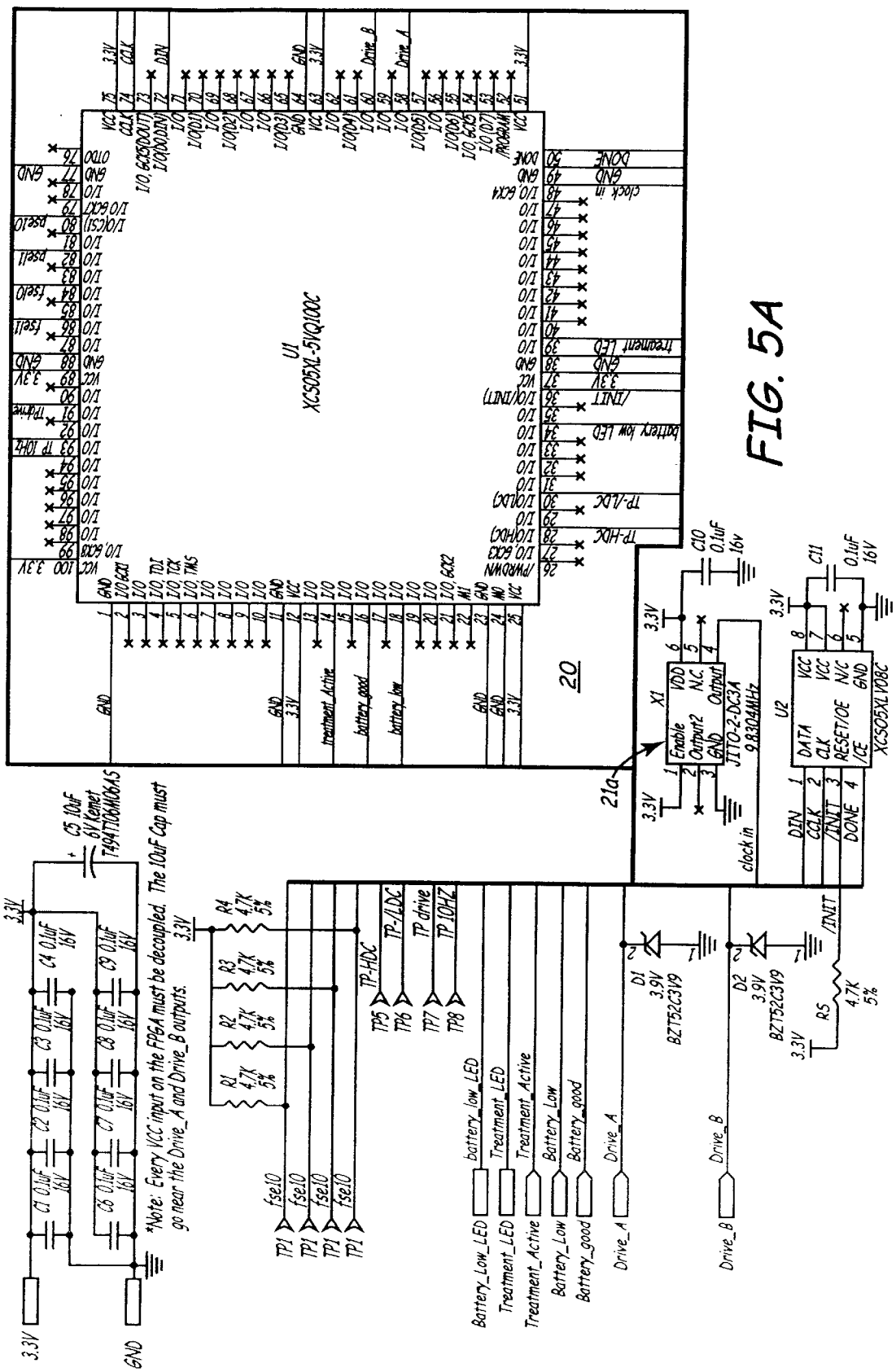
FIG. 5a illustrate overall connection of the aforesaid circuits through a gate array in the embodiment of FIG. 1.
Figure 6B:
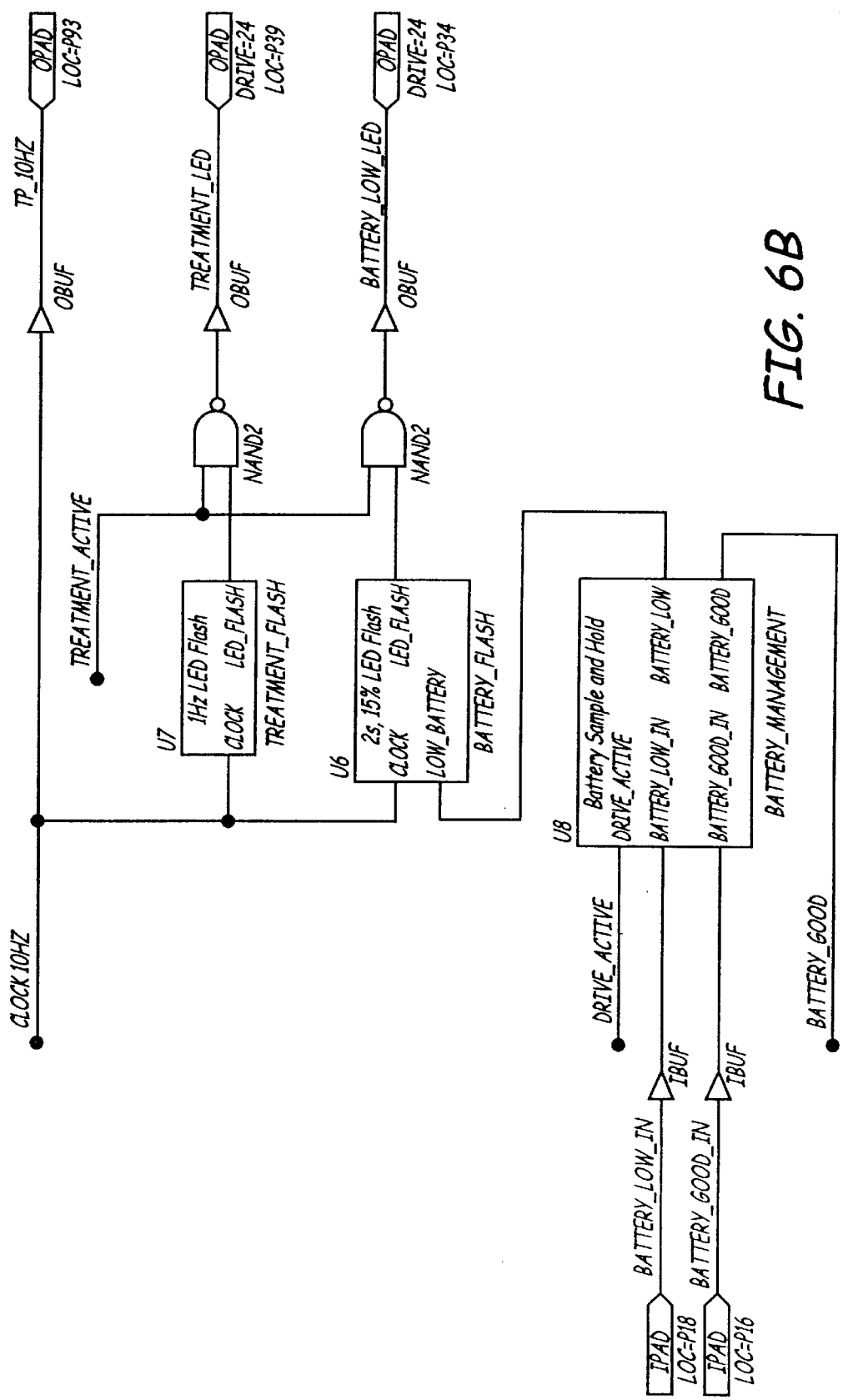

FIG. 5A illustrates the FPGA 20 and representative pin connections in the prototype embodiment. A local oscillator 21a provides a high frequency standard at 9.8304 MHZ, additional oscillators may be provided for the switching frequencies of the power supplies, or the transmission and switching frequencies may be synthesized from the basic high frequency. Preferably, however, the three frequencies are distinct, and the switching frequencies of the power supplies are all below the nominal transmission frequency, which may be, for example tuned to 5 MHz. In addition, the FPGA implements various software modules for creating a 10 KHz pulse control clock, a 10 Hz clock for applications such as treatment timeout or LED blinking control, and various timeout counters with periods of several microseconds to one hour for pulse, treatment or treatment regimen interval definition. In addition, the FPGA provides appropriate timing signals for battery sample and hold circuit to perform the voltage tests necessary for the battery indicator lights and overall battery management. Preferably the battery voltage is synchronously sampled just before the next current pulse; this helps assure that the sampled voltage is representative of the remaining battery life and is not artificially depressed by sampling during a transient current pulse. Overall logic for these operations is illustrated schematically in FIGS. 6A and 6B.

Thus, the overall construction of the external transmitter of the present invention involves a flexibly programmable control unit having low drive voltage requirements and operating flexibly to first provide an auto power down and power management system, and secondly, to define treatment pulses and synchronize operation a current-limited driver power supply and Class D amplifier with the defined pulse regimen so as to effectively deliver power to a tuned transmitter coil. This provides a programmed sequence of treatment pulses for nerve stimulation over an extended period of time using simple disposable batteries.

The invention being thus disclosed and described, variations and modifications of the invention, and adaptations of its features and advantages will occur to those skilled in the art, and such variations, modifications and adaptations are considered to be within the spirit and scope of the invention, as defined by the claims appended hereto and equivalents thereof.

What is claimed is:

1. A battery powered external power source for powering an implanted medical device having a receiver coil, of the type that inductively couples energy to the receiver coil through the skin of a patient, wherein the power source includes a first battery operated power supply and a second battery operated power supply, an FPGA powered by the first battery operated power supply, a class D amplifier powered by the second battery operated power supply, a local oscillator providing an input signal to the FPGA and, an antenna driven by the class D amplifier to inductively couple energy to the receiver coil, wherein the FPGA produces a modulation controlled pulse of RF frequency energy as an input for amplification by said amplifier to drive the antenna.

2. The battery powered external power source of claim 1, wherein the class D amplifier is coupled via holdup capacitors to the second power supply.

3. The battery powered external power source of claim 1, wherein the external antenna is sized to have a larger diameter than a receiver coil of the implanted medical device, and is tuned to resonate at the resonant frequency of the antenna of the receiver coil.

4. The battery powered external power source of claim 1, wherein said first and second power supplies are switching power supplies having different switching frequencies.

5. The battery powered external power source of claim 1, wherein said class D amplifier operates at a transmission frequency above several megahertz.

* * * * *